United States Patent
McGaffigan et al.

(10) Patent No.: US 6,638,275 B1
(45) Date of Patent: Oct. 28, 2003

(54) BIPOLAR ABLATION APPARATUS AND METHOD

(75) Inventors: Thomas H. McGaffigan, Saratoga, CA (US); Allan O. Mekailian, Hayward, CA (US)

(73) Assignee: Medironic, Inc., Minneapolis, MN (US)

( * ) Notice: Subject to any disclaimer, the term of this patent is extended or adjusted under 35 U.S.C. 154(b) by 0 days.

(21) Appl. No.: 09/684,376

(22) Filed: Oct. 5, 2000

(51) Int. Cl.⁷ ................................ A61B 18/18
(52) U.S. Cl. .................... 606/41; 606/46; 606/50; 607/101
(58) Field of Search .................. 606/41, 42, 45–50; 607/101, 102

(56) References Cited

U.S. PATENT DOCUMENTS

| | | |
|---|---|---|
| 5,531,676 A | 7/1996 | Edwards et al. ............. 604/22 |
| 5,542,915 A | 8/1996 | Edwards et al. |
| 5,667,488 A | 9/1997 | Lundquist et al. |
| 5,873,877 A * | 2/1999 | McGaffigan et al. .......... 606/41 |
| 5,964,756 A | 10/1999 | McGaffigan et al. .......... 606/41 |
| 5,976,129 A | 11/1999 | Desai ........................... 606/40 |
| 5,995,875 A * | 11/1999 | Blewett et al. ................ 607/98 |
| 6,016,452 A * | 1/2000 | Kasevich ...................... 606/41 |
| 6,106,521 A | 8/2000 | Blewett et al. |
| 6,325,798 B1 * | 12/2001 | Edwards et al. .............. 606/41 |

* cited by examiner

Primary Examiner—Linda C. M. Dvorak
Assistant Examiner—David M. Ruddy
(74) Attorney, Agent, or Firm—Thomas F. Woods

(57) ABSTRACT

A transurethral apparatus for radio frequency ablation treatment of the prostate having prostatic tissue of a human male having urethra which extends through the prostate comprising an elongate probe sized so that it is adapted to be introduced into the urethra and having a passageway extending therethrough. The elongate probe has proximal and distal extremities. Proximal and distal pairs of needle electrodes are provided which are carried by the distal extremity of the probe. A control mounted on the proximal extremity of the probe and extends through the passageway and is coupled to the proximal and distal pairs of needle electrodes for movement of the needle electrodes into and out of the prostate. A RF generator is provided for supplying RF energy to the needle electrodes for solely creating bipolar ablation with respect to the proximal and distal pairs of needle electrodes.

7 Claims, 8 Drawing Sheets

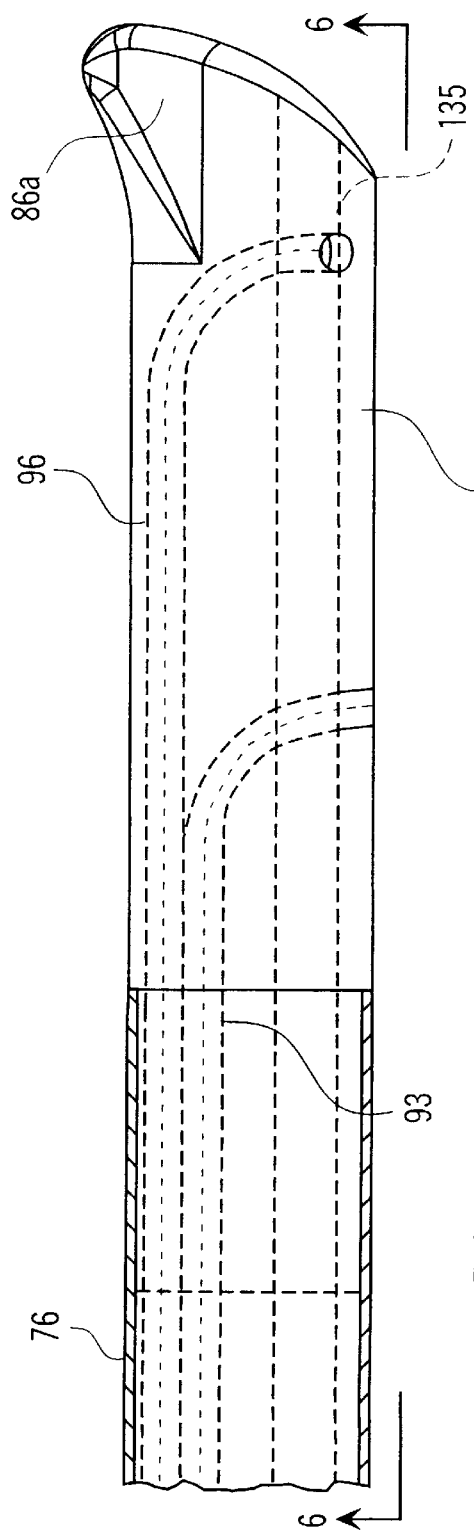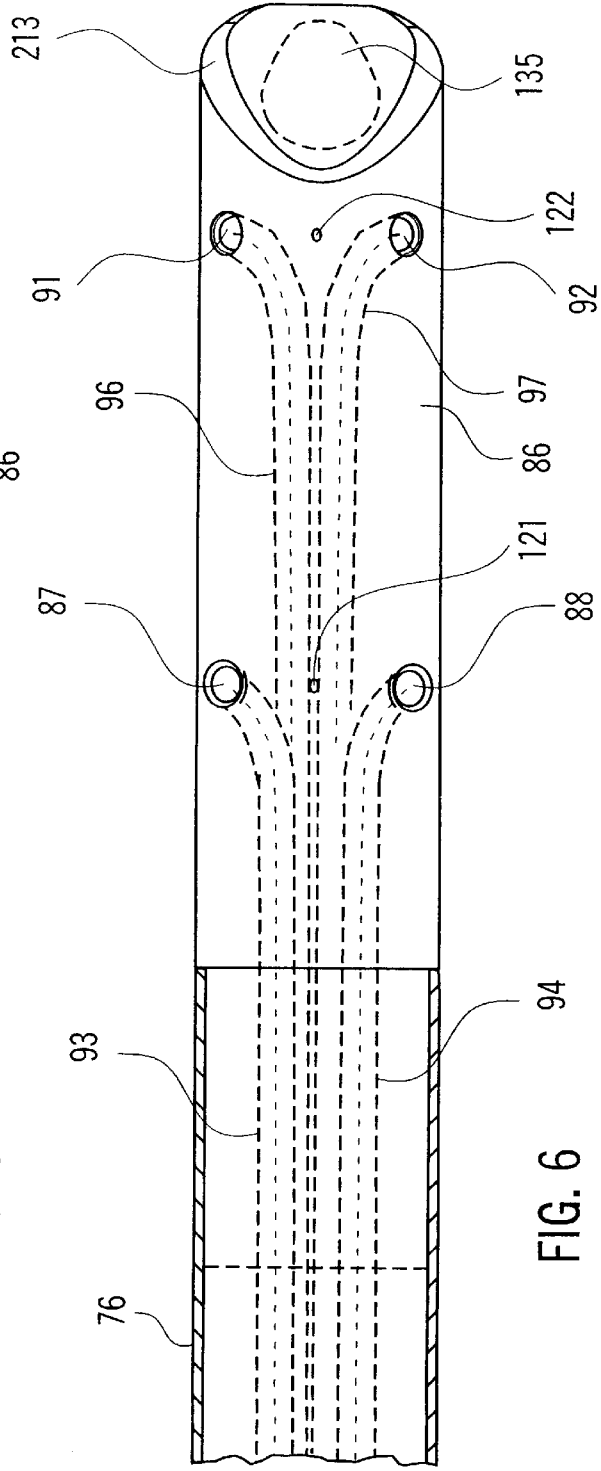
FIG. 5
FIG. 6

BIPOLAR ABLATION APPARATUS AND METHOD

This invention relates to a bipolar ablation apparatus and method.

Ablation apparatus has heretofore been provided for the ablation of prostatic tissue. Typically such apparatus has been comprised of two needles operating in unipolar mode with more than one deployment being utilized to obtain a lesion of the desired size in each lobe of the prostate. The use of multiple deployments for obtaining lesions of appropriate size ranges has resulted in unduly long procedure times. There is therefore a need for a new and improved apparatus and method for overcoming this deficiency as well as others.

In general, it is an object of the present invention to provide an apparatus and method which operates solely in the bipolar mode.

Another object of the invention is to provide an apparatus and method in which longitudinally spaced-apart needle electrodes are provided.

Another object of the invention is to provide an apparatus and method of the above character in which discrete pairs of needle electrodes are provided which are spaced apart longitudinally to provide proximal and distal pairs Another object of the invention is to provide an apparatus and method of the above character in which the pairs of needle electrodes are reconfigurable to obtain lesion formation of the desired size in the desired location with a single deployment.

Another object of the invention is to provide an apparatus and method of the above character in which lesions can be created in various directions extending from the needle electrodes.

Another object of the invention is to provide an apparatus and method of the above character in which it is possible to create a large lesion in a minimum amount of time.

Another object of the invention is to provide an apparatus and method of the above character in which overlapping lesions are created.

Another object of the invention is to provide an apparatus and method of the above character providing increased scope travel to permit viewing of the deployment of the needle electrodes.

Another object of the invention is to provide an apparatus and method of the above character in which impedance measurements are made and utilized to determine whether the capsule of the prostate has been perforated.

Another object of the invention is to provide an apparatus and method of the above character in which improved temperature sensing is provided.

Another object of the invention is to provide an apparatus and method of the above character in which temperatures are sensed in the needle electrodes.

Another object of the invention is to provide an apparatus and method of the above character in which higher power levels and faster lesion generation are made possible.

Another object of the invention is to provide an apparatus and method of the above character in which overall treatment times are substantially reduced.

Another object of the invention is to provide an apparatus and method of the above character in which the needle electrodes are provided with insulating sheaths and wherein the insulating sheaths are retracted upon deployment of the needle electrodes to expose distal extremities of the needle electrodes.

Another object of the invention is to provide an apparatus and method of the above character in which four-needle procedures can be accomplished followed by a two-needle procedure.

Another object of the invention is to provide an apparatus and method of the above character in which all electrical connections are made in an electrode needle slide.

Another object of the invention is to provide an apparatus and method of the above character in which a symmetrical irrigation arrangement is provided.

Another object of the invention is to provide an apparatus and method of the above character in which it is necessary to destroy four-needle operation capabilities in the apparatus prior to proceeding with a two needle operation.

Another object of the invention is to provide an apparatus and method of the above character in which when the two proximal needles have been deactivated, the filaments used for deactivation of those two proximal needles are destroyed to facilitate deployment of the remaining intact distal pair of needle electrodes.

Another object of the invention is to provide an apparatus which is economical to manufacture.

Additional objects and features of the invention will appear from the following description in which the preferred embodiments are set forth in detail in conjunction with the accompanying drawings.

FIG. 5 is an enlarged side elevational detail view of the distal extremity of the bullet-shaped tip of the elongate probe.

FIG. 6 is a bottom plan view looking along the line 6—6 of FIG. 5.

Figure 1:
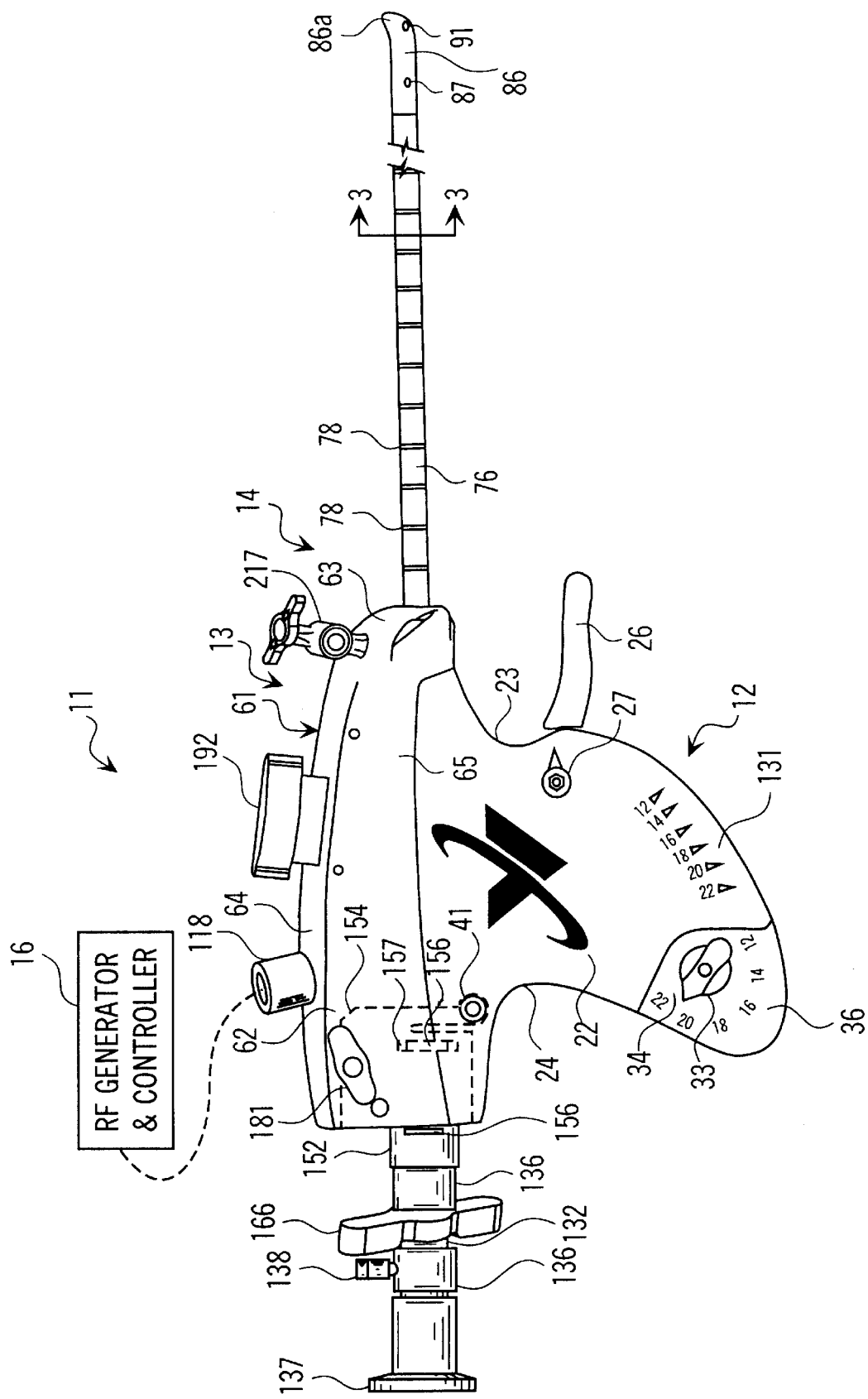
FIG. 1 is a side elevational view of a transurethral device and apparatus incorporating the present invention and showing the handle and removable cartridge providing a transurethral device.
Figure 2:
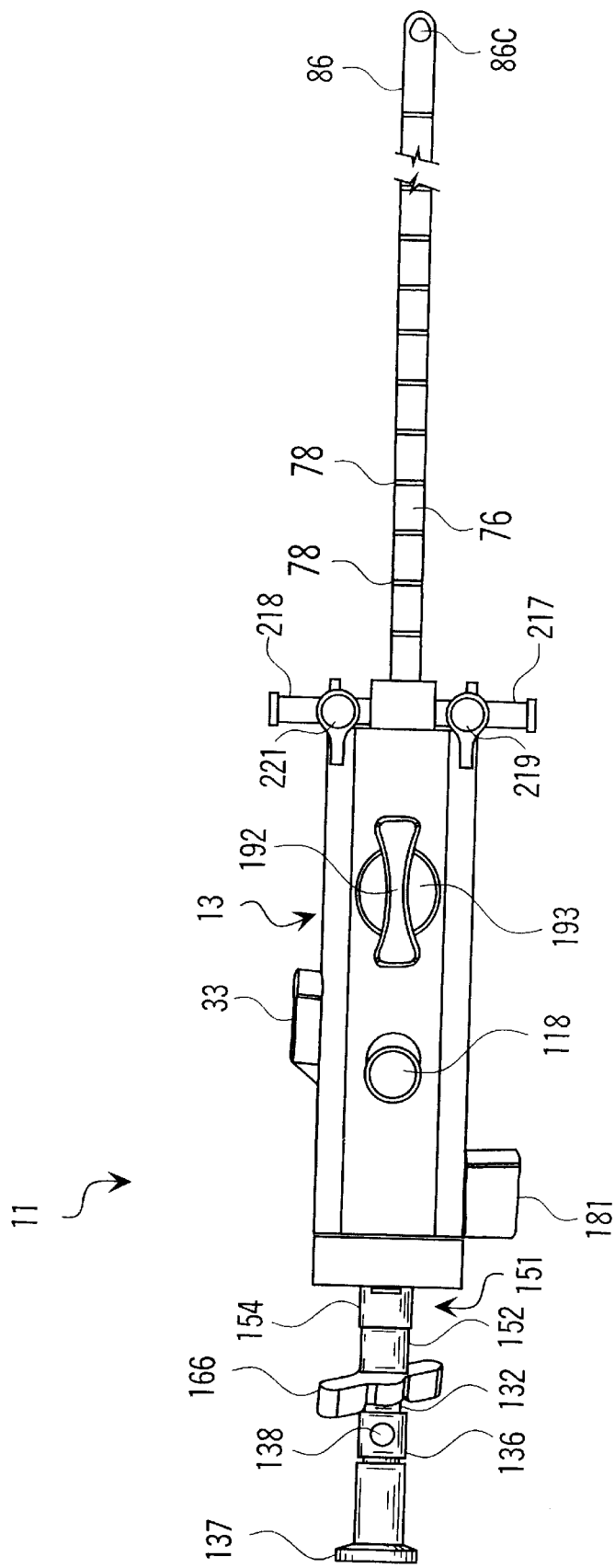
FIG. 2 is a top plan view of the device shown in FIG. 1.

In general, the transurethral apparatus of the present invention is for radio frequency ablation treatment of the prostate having prostatic tissue of a human male having a urethra extending through the prostate which comprises a transurethral device having an elongate probe sized so as to be adapted to be introduced into the urethra. The elongate probe has proximal and distal extremities and has a passageway extending therethrough from the proximal extremity to the distal extremity. Proximal and distal pairs of needle electrodes are carried by the distal extremity of the elongate probe. Means is mounted on the proximal extremity of the elongate probe and extends through the passageway of the elongate probe and is coupled to the proximal and distal pairs of electrodes for movement of the proximal and distal pairs into and out of the tissue of the prostate and including means for selectively applying radio frequency energy to the proximal and distal pairs of electrodes to cause bipolar ablation between pairs of electrodes selected from the proximal and distal pairs of electrodes.

More particularly as shown in the drawings, the transurethral apparatus 11 consists of a reusable handle 12 in which there is mounted a detachable cartridge 13 to provide a transurethral device 14. The device 14 is supplied with radio frequency energy from a radio frequency generator and controller 16. The radio frequency generator and controller 16 is a type which is commercially available from Vidamed, Inc. of Fremont, Calif., as Model 7600. Such a generator is provided with two channels of radio frequency energy, making it possible to deliver different amounts of power to two different needles which typically have been operated in a monopolar fashion utilizing a dispersive electrode adhered to the small of the back of the patient. In the present invention the needle electrodes are operated in a bipolar mode, eliminating the need for a dispersive electrode. Thus the two channels of the radio frequency generator provide four terminals identified as right and left active and right and left ground. These four terminals can be utilized in the present invention to operate in the bipolar mode with two different pairs of electrodes configured in three different patterns as hereinafter described with the active and ground terminals being continuously switched back and forth at a 475 KHz rate.

The handle 12 of the device 14 in many respects is similar to the handle disclosed in U.S. Pat. No. 5,964,756. Using that same construction, it is comprised of a housing 21 which is ergonomically shaped so as to be adapted to fit in the human hand. The handle 12 is in the form of a pistol grip which has a main body portion 22 that is provided with a forward indentation 23 adapted to receive the index finger of the human hand grasping the handle 12 and a larger rearwardly facing indentation 24 adapted to receive thumb of the same human hand.

The handle 12 is provided with an internal mechanism much the same as described in U.S. Pat. No. 5,964,756 and therefore will not be described in detail. This mechanism is adapted to be operated by a needle and sheath deployment and retraction trigger 26 that is adapted to be engaged by the forefinger of the hand holding the body portion of the housing 21. This trigger 26 is adapted to be moved from a "load" position indicated by the arrow 27 through a plurality of deployed positions indicated by the indicia 31 provided on opposite sides of the housing 21 ranging from 12 to 22 millimeters, indicating the length of penetration of the needle electrodes through the urethral wall and into the prostatic tissue of the prostate. Interconnected knobs 33 are provided on opposite sides of the housing 21 adjacent the lower extremity of the body 21 and have pointers 34 movable over indicia 36 ranging from 12 to 22 millimeters in the same increments as the indica 31 for setting stops for limiting movement of the trigger 26 so that overtravel beyond the setting provided by the knobs 33 cannot occur.

A release button 41 is provided on each of the opposite sides of the housing 21 for releasing the removable cartridge 13 in the manner hereinafter described.

The cartridge 13 consists of a cover 61 that is generally U-shaped in cross section and is formed of a suitable material such as plastic. The cover 61 is provided with proximal and distal extremities 62 and 63 and is formed by a curved top wall 64 and depending adjoining spaced-part parallel side walls 65. A guide rod 66 formed of a suitable material such as stainless steel is mounted in a fixed position within the cover 61 near the underside thereof having its distal extremity mounted in a front mounting block 67 and having its proximal extremity mounted in a rear mounting block 68. First and second slides 71 and 72 formed of a suitable material such as plastic and which also can be identified respectively as a needle electrode slide and a sheath slide are slidably mounted on the guide rod 66 in spaced-apart positions.

A flexible elongate rigid tubular torque member or probe 76 in the form of a torque tube formed of a suitable material such as stainless steel is provided and has its proximal extremity mounted in the front mounting block 67. The tubular torque member 76 can have a suitable diameter as for example 22 French and is provided with a passage 77 circular in cross section extending therethrough. The outer surface of the probe 76 is provided with spaced-apart markings 78 which are spaced apart by one centimeter increments to aid the physician in insertion of the probe 76 into the urethra.

A rigid optic tube 79 of a smaller size than the 22 French probe 76 as for example 18.5 French has its distal extremity mounted in the front mounting block 67 so that it is in alignment with the lower portion of the passage 77. The tube 79 is provided with a passage 81 which opens into passage 77. The tube 79 extends proximally in the cover 61 through recesses 82 and 83 provided in the needle slide 71 and the sheath slide 72, respectively, and has its proximal extremity mounted in a fixed position in the rear mounting block 68.

A bullet-shaped tip 86 formed of a suitable plastic transparent to light is secured to the distal extremity of the torque tube or probe 76 in the manner described in U.S. Pat. No. 5,964,756. As shown, the bullet-shaped tip 86 has an upturned rounded portion 86a. The elongate probe 76 and the tip 86 have a combined length of approximately 9.5 inches.

Figure 3:
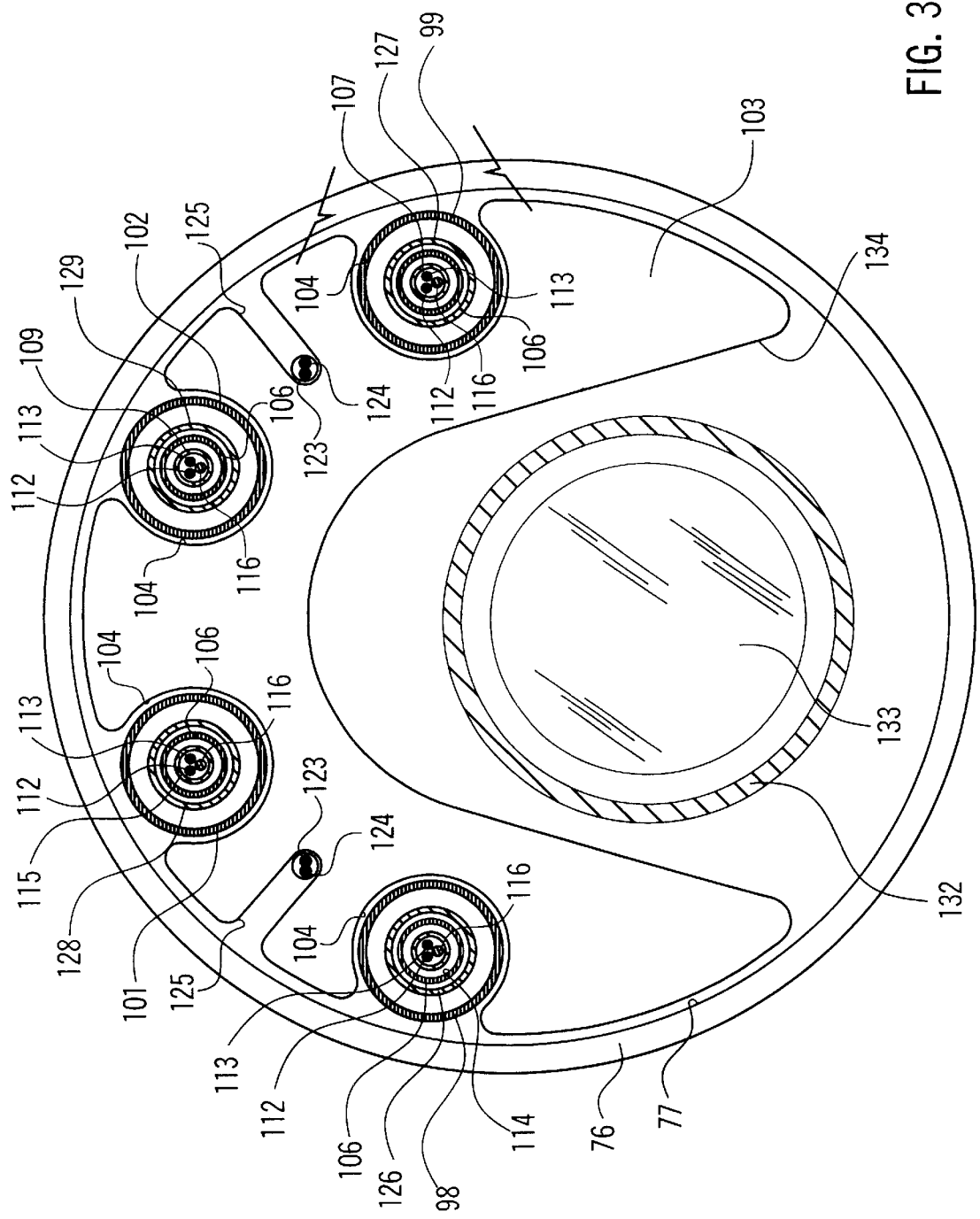
FIG. 3 is a greatly enlarged cross-sectional view taken along the line 3—3 of FIG. 1.
Figure 4:
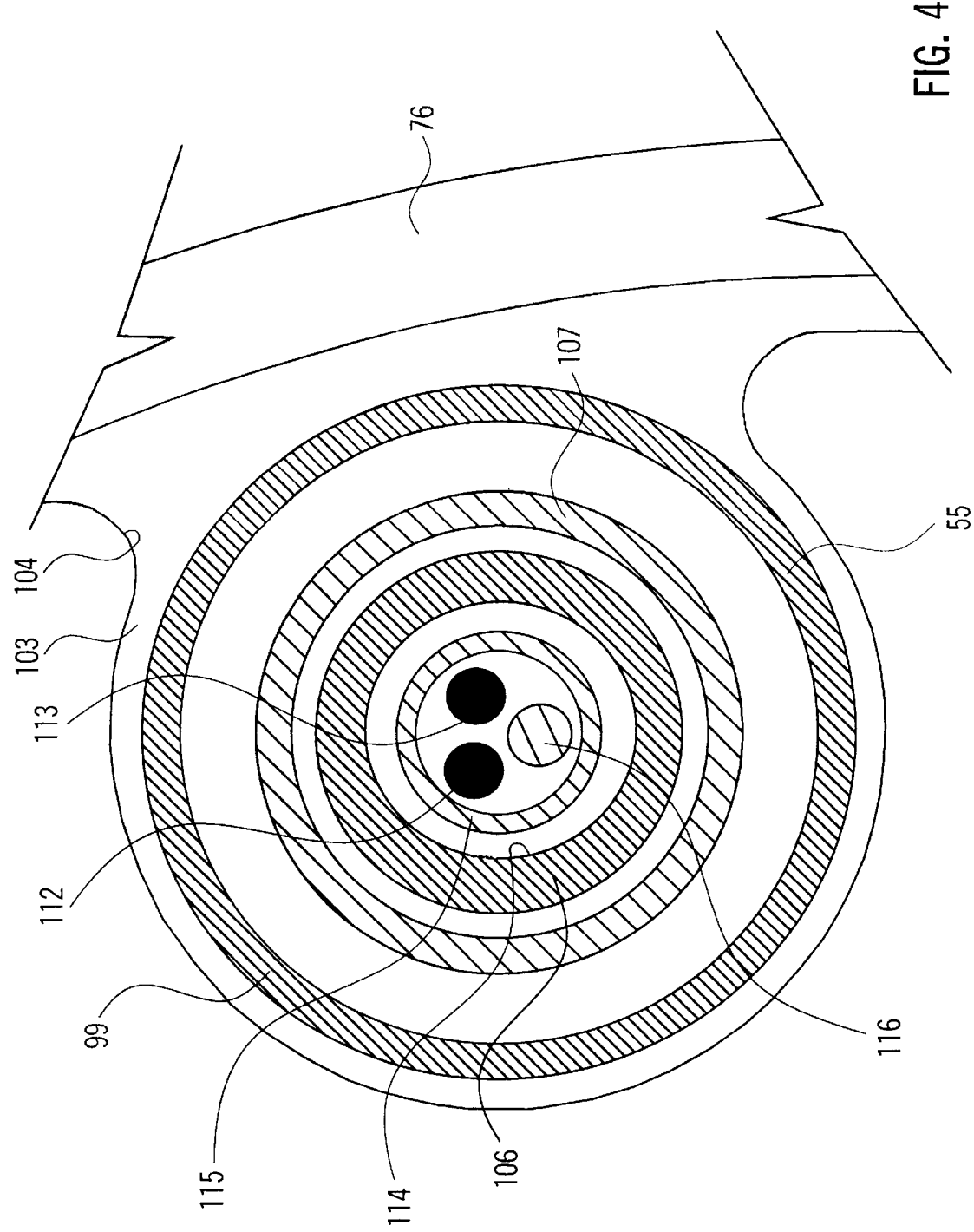
FIG. 4 is a still further greatly enlarged view showing a portion of the view shown in FIG. 3.
Figure 9:
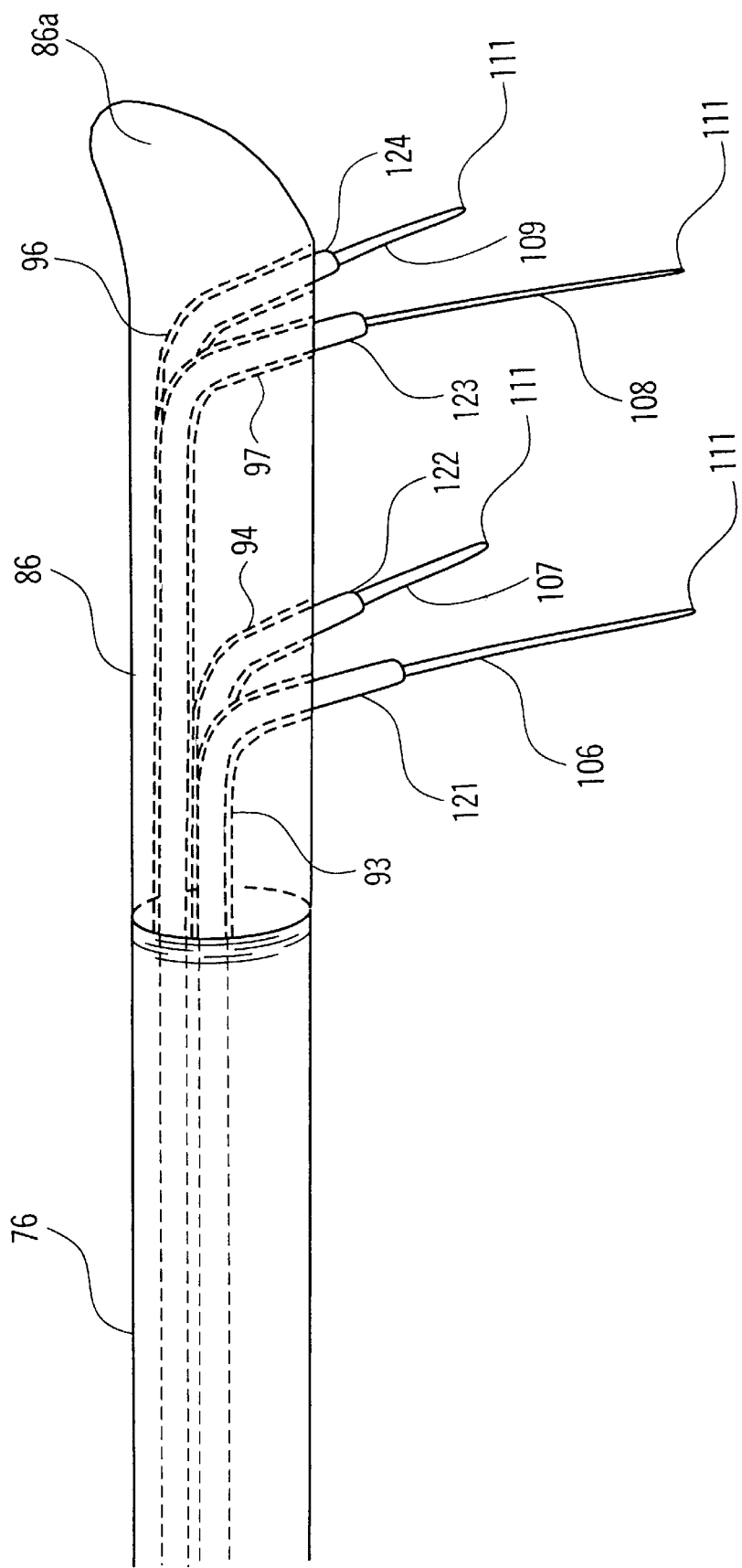
FIG. 9 is a side elevational view of the distal extremity of the elongate probe showing the proximal and distal pairs of needle electrodes as deployed.

A proximal pair of holes 87 and 88 and a distal pair of holes 91 and 92 are provided on the underside of the bullet-shaped tip 86 opposite the upturned portion 86a. The holes 87 and 88 are spaced apart from each other by a suitable distance as for example one centimeter, which dimension is basically determined by the diameter of the torque tube 76. Similarly, the distal pair of holes 91 and 92 are also spaced apart approximately one centimeter but as shown in the drawing, the distal pair of holes is slightly more closely spaced (see FIG. 9) than is the proximal pair of holes 87 and 88 for reasons hereinafter described. Angled guide tubes 93 and 94 which are aligned with the proximal holes 87 and 88 and angled guide tubes 96 and 97 which are aligned with the distal holes 91 and 92 have L-shaped 90° bends therein that are molded into the transparent bullet-shaped tip 86. The 90° bends provided in these angled guide tubes 93, 94, 96 and 97 provide transitions from movement through the tubes along a longitudinal axis to movement along a transverse axis extending at 90° with respect to the longitudinal axis. The angled guide tubes 93, 94, 96 and 97 adjoin straight guide tubes 98 and 99 and 101 and 102, respectively, which extend through the passage 77 provided in the torque tube or elongate probe 76 and extend proximally into the front mounting block 67 and extend out of the torque tube 76 and terminate immediately above the optic tube 79 at the proximal extremity of the front mounting block 67. As shown particularly in FIG. 3, the guide tubes 98 and 99 and 101 and 102 are supported in predetermined spaced-apart positions in the passage 77 by an insert 103 formed of plastic disposed in the torque tube 76 having spaced-apart recesses 104 formed in the outer periphery of the insert 103.

A proximal pair of needle electrodes 106 and 107 are slidably mounted in the guide tubes 98 and 99 and a distal pair of needle electrodes 108 and 109 are slidably mounted in the guide tubes 101 and 102 and the guide tubes 96 and 97. In accordance with the present invention, the needle electrodes are formed of a hollow superelastic nickel-titanium material having an outside diameter of 0.018" and inside diameter of 0.012" and a wall thickness of 0.003". The distal extremity of each of the needle electrodes is provided with a sharpened tip and has thermocouple 111 mounted within the sharpened tip. Each thermocouple is provided with a pair of wires 112 and 113 which extend proximally from the sharpened tip through the needle electrodes through lumens 114 provided in the hollow needle electrodes. A separate insulating sleeve 115 is provided in each of the lumens 114 to provide additional insulation isolating the thermocouple wires from the metal needle electrodes. Also in order to strengthen the needle electrodes 106–109 and to prevent wall collapse and kinking during bending, a nickel-titanium rod 116 having a diameter of 0.006" is placed within each insulating sleeve 115 alongside the thermocouple wires 112 and 113 having an outside diameter of 0.005". The rod 116 and the thermocouple wires 112 and 113 are cemented in place by a suitable polyurethane adhesive (not shown). The proximal extremities of the needle electrodes 106, 107, 108 and 109 are secured to the needle slide 71 so that they move therewith. Thus all four of the needle electrodes 106, 107, 108 and 109 are secured to the needle slide 71 and the thermocouple wires 112 and 113 connected thereto are connected to terminals 117 provided on the needle slide 71. The terminals 117 are connected to a flex circuit tape 118 which connects the needle electrodes 106, 107, 108 and 109 as well as the thermocouple wires 112 and 113 mounted therein to a 14-terminal connector 119 mounted in the cover 61.

In connection with the present invention it has been found that the optimum spacing between the proximal and distal pairs of needle electrodes is approximately 1.5 centimeter. Although larger spacings can be utilized, it has been found that the lesions formed are not optimum because they assume an hourglass shape. With respect to the distances between two pairs of needle electrodes it has been found that a W/L aspect ratio of 1:1.5 can be tolerated since a 50% change in impedance only occurs when switching from one designated pair to another. Thus the impedance can range from 100 ohms to 150 ohms with the understanding that the acceptable impedance range for the RF generator and controller 16 is approximately 400 ohms maximum. Impedance sensing is provided to determine when the capsule of the prostate has been perforated.

Thermocouples 121 and 122 are encapsulated in the bullet-shaped tip 86 (see FIG. 9) and are disposed midway respectively between each pair of openings 87 and 88 and openings 91 and 92 and are provided for sensing urethral wall temperatures. Each of the thermocouples 121 and 122 are connected to wires 123 and 124 extending through the passage 77 and being supported in recesses 125 in the insert 103 and being connected through terminals 117 and the flexible tape 118 to the connector 119. The thermocouples 121 and 122 are used to ensure that the highest temperature reached in the urethra does not exceed 47° C. The hottest location is found to be between the needle pairs with each pair having an included angle of approximately 40° and it is for this reason that the thermocouples 121 and 122 are so located.

Insulating sheaths 126, 127, 128 and 129 formed of a suitable insulating material are coaxially and slidably disposed on the needle electrodes 106, 107, 108 and 109 and have their proximal extremities secured to the sheath slide 72 so that they move therewith. The insulating sheaths 126, 127, 128 and 129 extend through the guide tubes 98, 99, 101 and 102 so that the entire lengths of the needle electrodes 106, 107, 108 and 109 extending through the passage 77 are insulated from each other and from the torque tube 76. As hereinafter explained, the insulating sheaths are sized in length so that when the needle electrodes are retracted within the bullet-shaped tip 86, they are covered with the insulation and when deployed continue to cover the needle electrodes. The sheaths provide additional stiffness to the needle electrodes during penetration of the urethral wall but after penetration into the tissue of the prostrate, the sheaths are retracted a predetermined amount as for example 6 millimeters so that there are exposed approximately 6 millimeters of the needle electrodes in the tissue of the prostate with the insulating sheaths still extending through the urethral wall so as to protect the urethral wall during RF ablation of prostatic tissue.

The optic tube 79 and the torque tube 76 are sized to receive a conventional telescope or scope 131 which includes a tubular member 132 that includes rod lenses 133 and fiber optics (not shown) surrounding the rod lenses. The scope 31 is movable through the passage 81 provided in the optic tube 79 and through a longitudinally extending recess 134 generally V-shaped in cross section in the insert 103 in the passage 77 of the torque tube 76 and thence into a bore 135 provided in the bullet-shaped tip 86. The bore 135 is in alignment with the recess 133 provided in the torque tube 76. When the distal extremity of the tubular member 132 is positioned within the bore 134, it is possible to view the surrounding region through the transparent bullet-shaped tip 86 because the tip 86 has an index of refraction which is similar to the surrounding liquid as for example a saline solution.

A fitting 136 is provided on the proximal extremity of the tubular member 132 and includes an eyepiece 137 and a connector 138 for making connection to a fiber optic light source (not shown).

In order to permit movement of the scope 131 into position so that the physician can also observe independently deployment of the distal and proximal pairs of needle electrodes, means is provided for causing longitudinal movement of the scope 131 relative to the torque tube 76. To this end telescope moving means 146 is provided in the rear mounting block 68. The rear mounting block 68 is provided with spaced-apart depending arms 147 which are adapted to extend downwardly into the handle 12 and into engagement with the release buttons 41 and to yieldably urge them outwardly and retain the cartridge 13 on the handle 12. Upon compression of the release buttons 41 by the hand, the depending arms 147 are released, permitting the cartridge 13 to be separated from the handle 12. A retaining pin 148 extending through the side walls of the housing 21 of the cartridge and through the rear mounting block 68 serves to retain the rear mounting block within the housing 21 of the cartridge 13.

The telescope moving means 146 comprises a telescoping assembly 151 consisting of first, second and third parts 152, 153 and 154 which also can be identified as distal, intermediate and proximal parts which are telescopically mounted with respect to each other. The intermediate part 153 is telescopically mounted in the first or distal part 152 and the third or proximal part 154 is telescopically mounted in the second or intermediate part 153. The parts 152, 153 and 154 can be formed of a suitable material such as plastic and are rectangular in cross section. The first or distal part 152 is provided with exterior outwardly extending ears 156 which seat in slots 157 provided in the rear mounting block 68. The intermediate part 153 is slidably mounted in the distal or first part 152 and is provided with an outwardly extending rim 158 which is adapted to engage an inwardly extending rim 162 of the intermediate part to prevent telescoping movement of the second or intermediate part 153 out of the first or distal part 152 (see FIG. 7). The third or proximal part 154 is slidably mounted in the intermediate part 153 and is also provided with an outwardly extending rim 161 which is adapted to engage an inwardly extending rim 162 of the intermediate part to prevent telescoping movement of the proximal part 154 out of the intermediate part 153.

A telescoping mating protrusion 163 which has a bore 164 extending therethrough for receiving the scope 131 is formed on the proximal extremity of the proximal or third part 154. A scope locking lever 166 is rotatably mounted on the protrusion 161 and is movable between telescope locking and unlocking positions in a manner well known to those skilled in the art.

Figure 7:
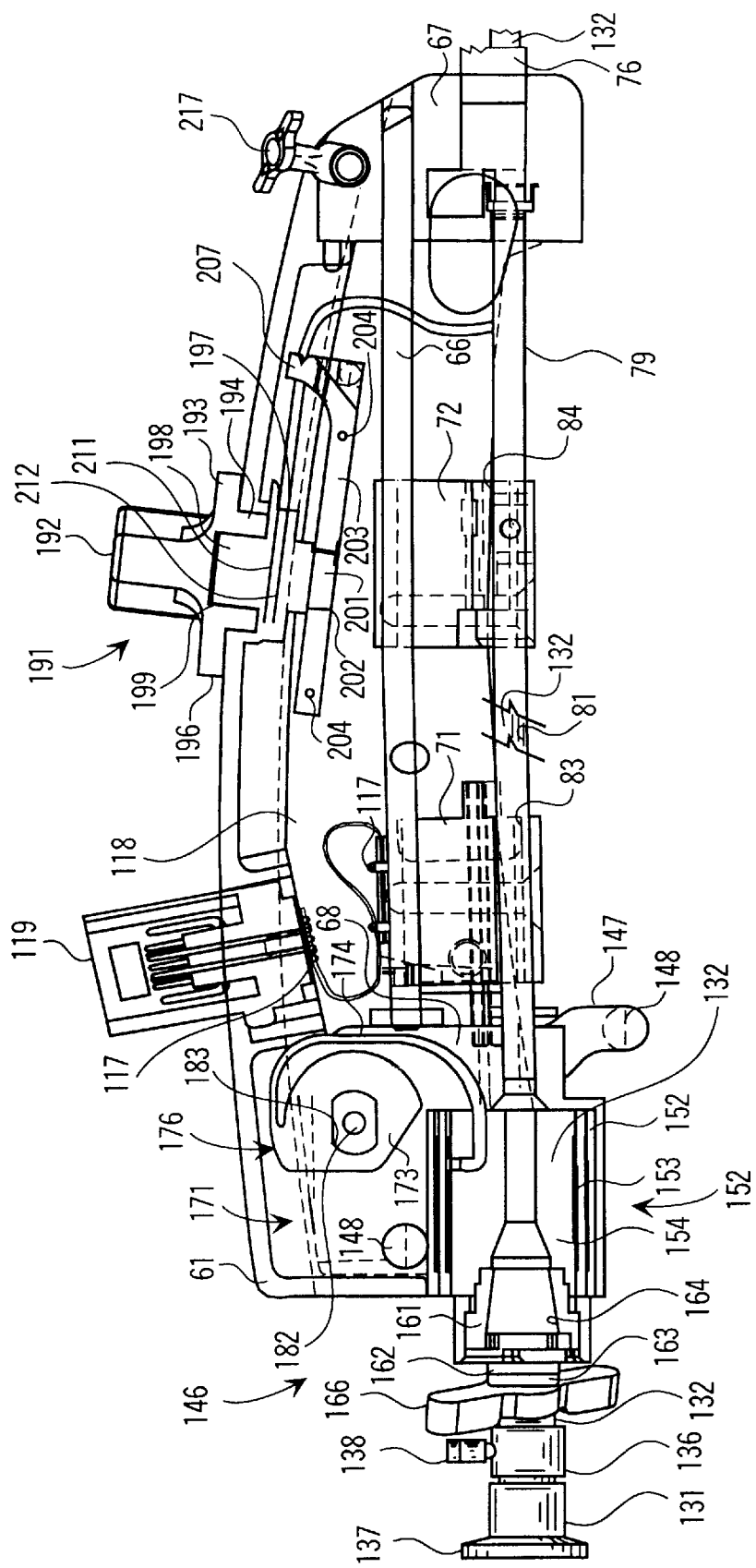
FIG. 7 is an enlarged detail view of the cartridge shown in FIGS. 1 and 2 with certain parts in cross section and showing the telescope moving means with the telescope in a retracted position.
Figure 8:
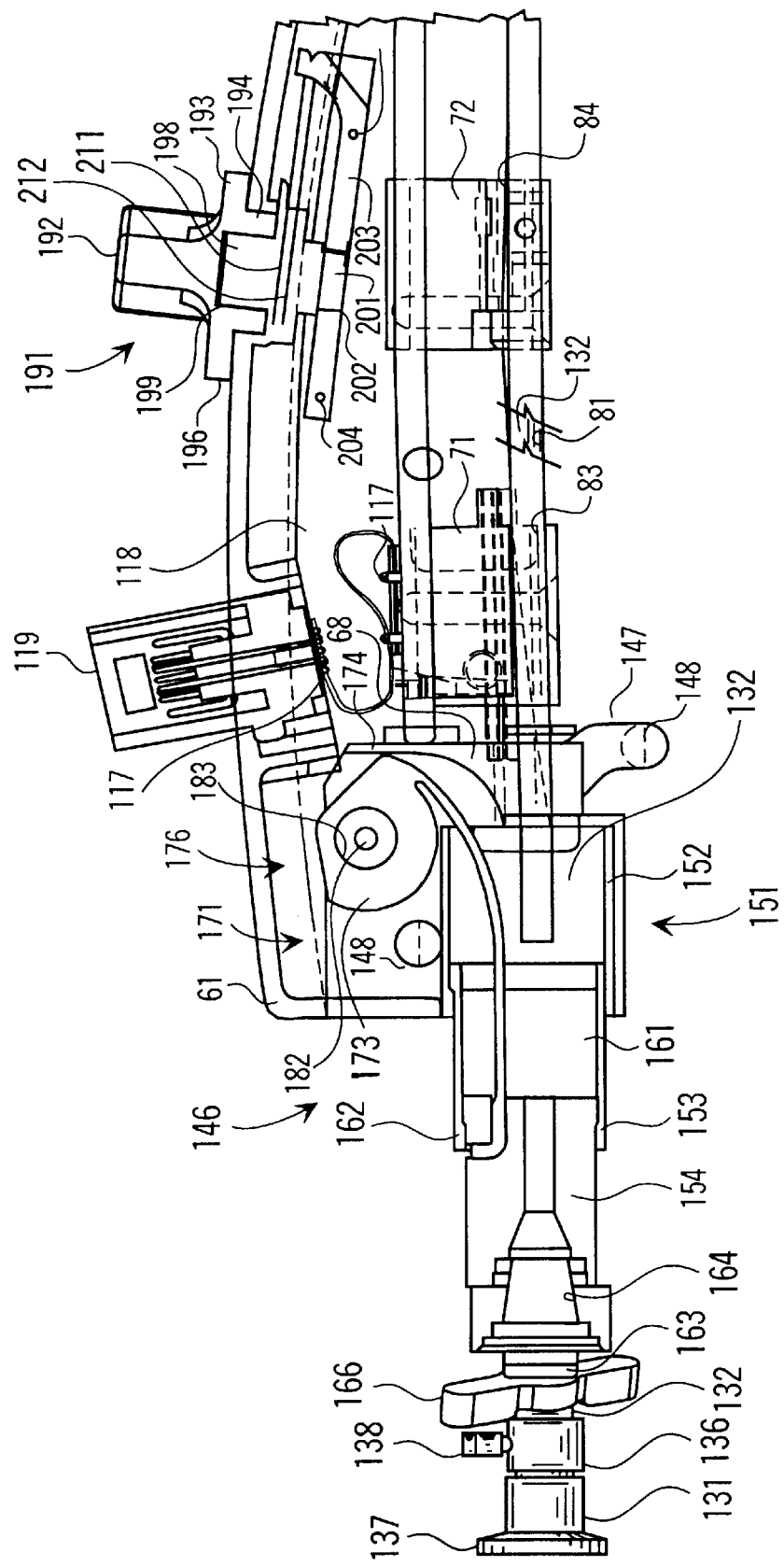
FIG. 8 is a partial view corresponding to FIG. 7 but showing the telescope moving means with the telescope in an advanced position.

The telescope moving means 146 also includes a scroll mechanism 171 for operating the telescoping assembly 151 and consists of a scroll 172 formed of a suitable material such as Nylon which has a rigid central core 173 and a flexible strip 174 integrally formed therewith which has rigidity in a lateral direction and stiffness along its length. The distal extremity of the strip 174 is mounted in an L-shaped slot 176 provided in the distal or third part 154. A telescope positioning knob 181 is provided which is accessible from the exterior of the housing 21 of the cartridge 13 and has a shaft 182 extending through the housing and through a bore 183 in the core 173 with the shaft 182 and the bore 183 being cooperatively engaged so that as the shaft 182 is rotated, the scroll 172 is rotated. The scroll 172 can have a suitable width as for example ⅜" with the flexible strip 174 having a similar width of ⅜" and having a suitable thickness as for example 0.040" so that the flexible strip 174 can be rolled and unrolled and yet be stiff enough to advance and retract the telescope 131 carried by the telescoping assembly 151 as shown in FIGS. 7 and 8.

The telescope moving means 146 provided is advantageous in that it provides sufficient travel to permit viewing of the proximal and distal needle electrode pairs independently of each other as hereinafter described.

Means is provided for converting the device from a four-needle configuration to a two-needle configuration by use of a conversion mechanism 191. The conversion mechanism 191 consists of a knob 192 rotatably mounted on the cover 61 adapted to be grasped by the fingers of the hand. The knob 192 is provided with a circular flange 193 which overlies the cover 61 and has a boss 194 extending through a hole 196 provided in the cover 61. A rotatable cam 197 is provided which has a first boss 198 which is mated with a recess 199 provided in the boss 194 so that a driving relationship is formed between the boss 194 and the boss 198 whereby as the knob 192 is rotated, the rotatable cam 197 is rotated. The rotatable cam 197 is also provided with a cylindrical boss 201 which is disposed within a bore 202 provided in a plate 203 within the cover 61. The plate 203 is provided with ears 204 on opposite sides which extend through spaced-apart holes 206 provided in each of the opposite side walls 65 so that the plate 203 is firmly supported in a fixed position with respect to the top wall 64 of the cover 61.

The plate 203 is provided with an upturned distal extremity 207 which has a pair of spaced-apart upwardly opening slots 208 which receive two flexible filaments 211 and 212 formed of a suitable material such as Nylon which have their ends affixed to the rotatable cam 197. The other ends of the filaments 211 and 212 extend distally and downwardly and have their distal extremities secured to the proximal needle electrodes 106 and 107 and their insulating sheaths 121 and 122 by as for example punching holes (not shown) in the filaments 211 and 212 and having those needle electrodes and insulating sheaths extend therethrough. As hereinafter explained, in converting from four-needle to two-needle operation, the rotation of the knob 122 causes the filaments 211 and 212 to be wrapped onto the cam 197 and to pull the same upwardly and to cause irreversible buckling of the proximal needle electrodes 106 and 107 with their insulating sheaths 121 and 122. Once the buckling operation has been completed, the filaments 211 and 212 snap and break off so they do not interfere with the subsequent deployment of the remaining intact distal pair of needle electrodes and sheaths.

When a switch is made to the two-needle mode of operation as hereinafter described, there is still a thermocouple 122 between the distal pair of needle electrodes while they are being used. This ensures that the urethral wall temperature is still being measured when switching to a two-needle mode of operation. An over-temperature reading from thermocouples 121 or 122 shuts down the operation of the apparatus 11.

Symmetrical irrigation means 216 is provided for supplying an irrigating liquid as for example a saline solution to the device 14 during an ablation procedure and consists of first and second one-way stop cocks 217 and 218 carried on opposite sides of the distal extremity of the cover 61 and mounted in the front mounting block 67. The stop cocks 217 and 218 are provided with knobs or handles 219 and 221, respectively, for moving the stop cocks between open and closed positions to control the supply of irrigating liquid to and from the elongate probe 76 and to control the aspiration of liquid. The front mounting block 67 is provided with flow passages (not shown) communicating with the stop cocks 217 and 218 and the passage 77 provided in the probe which is in communication with a bore 226 provided in the bullet-shaped tip 86 and extending therethrough so that the irrigation liquid being supplied is discharged from the distal extremity of the bullet-shaped tip and surrounds the bullet-shaped tip so as to permit viewing of the needle electrodes as they are deployed as hereinafter described. The use of the two stop cocks 217 and 218 makes it possible to supply irrigation liquid through one stop cock and aspirate through the other stop cock or alternatively through the common flow passage 71 in the probe 76 and the bore 226 in the tip 86.

Operation and use of the transurethral apparatus 11 may now be briefly described as follows. Let it be assumed that the device 14 has been assembled and that the scope 131 has been inserted and locked in place and connected to a fiber optic source of light. Similarly let it be assumed that the RF generator and controller 16 has been connected to the connector 118. Let it also be assumed that an irrigation liquid source has been connected to one of the stop cocks as for example stop cock 217 and that an aspiration source has been connected to the other stop cock 218.

Let it also be assumed that it is desired to ablate the prostate of a patient who has previously been examined to determine the size of the prostate. The physician having this information selects the desired length of the needle penetration by adjusting the knob 33 to the appropriate dimension as for example 18 millimeters. The scope 131 is advanced to its forwardmost position by rotation of the knob 181 in a clockwise direction so that the distal extremity of the tubular member 132 is advanced into the bore 133 in the bullet-shaped tip 86. Assuming that the patient has been properly prepared for the procedure, the probe 76 is inserted into the urethra of the penis of the patient with the physician grasping the body portion 22 of the handle 12 with the forefinger being disposed above the trigger 26 and the thumb being positioned in the indentation 24. The advancement of the device 14 is observed by the physician holding his eye against the eyepiece 137. During this advancement, the knobs 219 and 221 of the stop cocks 217 and 218 are operated to supply an irrigating solution as for example a saline solution exiting through the bullet-shaped tip so that the physician is provided with a clear view of the urethra as the elongate probe 76 is being advanced. Typically an irrigation flow rate of 125 cubic centimeters per minute minimum is provided. When desirable, the supply of irrigation liquid can be terminated by closing stop cock 218. When and if necessary, liquid can be aspirated from the distal extremity of the elongate probe 76 by opening the stop cock 218 to withdraw aspirate through the flow passage 77. As typical in such a procedure, the elongate probe 76 is advanced until the bullet-shaped tip 86 has been advanced into the bladder of the patient. Thereafter, the elongate probe 76 is withdrawn by approximately one centimeter to properly position the bullet-shaped tip 86 in the vicinity of the prostate gland of the patient. The depth of penetration of the elongate probe into the urethra can be gauged by observing the one centimeter spaced-apart markings 78 provided on the exterior surface of the probe. The angular position of the probe in the urethra can also be gauged by observing the upturned portion 86a of the bullet-shaped tip 86 and the holes 87–92 so that the probe is positioned in the proper angular position to treat the desired side lobe of the prostate. The physician then rotates the telescope positioning knob 181 to retract the scope 131 so that the distal extremity is immediately to the rear of the distal holes 91 and 92 provided in the bullet-shaped tip 86 so as to make it possible for the physician to view the deployment of the distal pair of needle electrodes 108 and 109. Alternatively, if desired the scope 131 can be further retracted so that it is immediately to the rear of the proximal holes 87 and 88 so as to permit viewing simultaneously the deployment of both pairs 106 and 107 and 108 and 109 of needle electrodes. Alternatively, the physician can move the telescope back and forth by operation of the knob 181 to permit viewing of the two pairs of electrodes by observing individually each of the two pairs or observing the pairs being deployed in unison or at the same time.

After the elongate probe 76 has been properly positioned, the physician utilizes the trigger 26 to bring it downwardly along the handle 12 to cause advancement in unison of the needle electrodes and their sheaths to cause them to pass out of the holes 87-92 and to penetrate the urethral wall. This penetration of the urethral wall can be readily observed by the physician using the eyepiece 137 of the scope 131. If the physician is satisfied with the deployment of the needle electrodes through the urethral wall, deployment of the needle electrodes is continued by further pulling down on the trigger 26 until the desired penetration as selected by the knob 33 has been reached. The mechanism within the handle prevents the trigger 26 from being moved beyond the marking selected by the knob 33 as for example the six millimeters marking hereinbefore described. The mechanism within the handle has been hereinbefore described in U.S. Pat. No. 5,964,756. As described therein, advancement of the trigger 26 causes the needle electrodes to advance into the prostatic tissue. After the urethra has been penetrated by both the needle electrodes and the insulating sheaths and at or near the end of the movement of the needle electrodes into the prostatic tissue, the insulating sheaths are retracted a predetermined amount as for example approximately six millimeters to expose the distal extremities of the needle electrodes in the prostatic tissue while at the same time retaining the insulating sheaths so they extend beyond the urethral wall to protect the urethral wall from ablation during ablation of the prostatic tissue.

As soon as the movement of the trigger 26 is stopped, this indicates to the physician that the needle electrodes have been deployed to the desired depth and into the prostatic tissue of the lobe being treated. The radio frequency generator and controller 16 is then placed in operation by the physician to supply radio frequency energy to the needle electrodes for a suitable period of time as for example for approximately five minutes at ten watts of power.

By using such a four-needle arrangement, it has been found that it is possible to complete an entire treatment of a lateral lobe with a single deployment. Typically the proximal and distal pairs of the four needles are spaced apart by 1.5 centimeter for treating a 2 to 2.5 centimeters long lateral lobe which is the typical length for human males. If an uncommon longer lateral lobe is being treated, it may be desirable to utilize an additional deployment. This can be accomplished by retracting the needle electrodes and by moving the trigger 26 in an upward position to its home position indicated by the arrow 27 and thereafter advancing the probe longitudinally a suitable distance as for example for one to two centimeters and then redeploying the needle electrodes in a manner hereinbefore described and then reapplying radio frequency energy to the electrodes for a similar time and power level to complete the formation of the desired size lesion or lesions in the lateral lobe. Any possible overlap of such lesions does not create a problem.

In the formation of such lesions, a lesion is created around each of the needles and also between the needles because of the bipolar operation. Thus, typically a lesion is created which extends 0.5 centimeter beyond each of the four needle electrodes and also encompasses the area in between the needle electrodes to create a large lesion in the prostatic tissue. There is no overheating in the area of overlap.

The ablation procedure is precisely controlled by making temperature measurements with the needle thermocouples 111 positioned at the distal extremities of the needle electrodes. Thus the temperatures being measured are in the prostatic tissue immediately surrounding the needle electrodes to provide a rapid temperature response.

When the desired ablation has been carried out in one of the lateral lobes and it is desired to treat the other of the lateral lobes, the needle electrodes are retracted by moving the trigger 26 upwardly to its home position indicated by the arrow 27. Thereafter, the elongate probe 76 can be rotated to reposition the bullet-shaped tip 86 so that the side holes 87–92 are in general registration with the other side lateral lobe. The needle electrodes can then again be redeployed by operation of the trigger 26 in the manner hereinbefore described to advance the needle electrodes into the prostatic tissue. Thereafter, radio frequency energy can be supplied to the needle electrodes to carry out the desired ablation under the control of the RF generator and controller 16. After this lateral lobe has been appropriately treated, the device 14 can be withdrawn and the supply of irrigation liquid terminated to terminate the procedure.

However, in approximately 20 to 25% of the patients being treated for BPH, it is necessary to also treat the medial lobe. Since the medial lobe is substantially smaller than the two lateral lobes, the four-needle configuration provided by the device encompasses too much area and therefore it is necessary to deactivate one of the two needle electrode pairs. This is accomplished in the present device by rotating the knob 192 of the conversion mechanism 191 in a clockwise direction which causes tensioning of the filaments 211 and 212 by winding the same onto the rotatable cam 197. This causes kinking of the guide tubes 98 and 99 to such an extent they are irreversibly buckled so that the buckled portions form sharp angle vees with the legs of the vee being in close proximity to each other, or in other words so that they are substantially parallel to each other. This in effect destroys the rear or proximal pair of needle electrodes so they can no longer be activated. This is not disadvantageous because prior hereto all of the four needle procedures have been accomplished by treating the two lateral lobes and all that remains to be treated is the medial lobe. The cartridge 13 is intended to be a cartridge of one-time use and therefore the disablement of the rear or proximal pair of electrodes is not undesirable since the cartridge 13 will no longer be used after the BPH ablation procedure has been completed on that patient.

After the rear or proximal pair of needle electrodes has been deactivated in the manner hereinbefore described, the probe can again be positioned so that the remaining distal needle pair is positioned so that it is in registration with the medial lobe of the prostate. As soon as this has been accomplished, the remaining distal pair of needle electrodes can be deployed into the prostatic tissue of the medial lobe by pulling the trigger 26 downwardly to the desired depth of penetration. Radio frequency energy is then supplied from the RF generator and controller 16 to perform the desired ablation in the medial lobe. If necessary, an additional deployment of the distal pair of electrodes can be accomplished by first withdrawing the needle electrodes, advancing or retracting the probe, and then redeploying the distal pair of electrodes and supplying the radio frequency energy thereto. After the medial lobe has been treated, the distal pair of needles can be retracted by raising of the trigger 26, after which the irrigation liquid can be terminated and the device 14 removed from the urethra to complete the procedure.

In accordance with the operation of the apparatus 11 of the present invention it has been found that during the ablation procedure the amount of power required to heat tissue in the prostate to a target temperature ranging from 100° C. to 110° C. varies with each needle. It is undesirable to exceed approximately 100° C. in the tissue because at that temperature water vapor is created which can surround the needle and cause a high impedance to occur which will terminate the electrical conductivity between the needle and the surrounding prostatic tissue. In addition it has been found that the thermal load on the proximal or rear set of needle electrodes is approximately twice the thermal load provided by the distal pair of needle electrodes.

In the preferred procedure in the present invention, it has been found desirable when operating with the two channel RF generator and controller 16 to ramp up to full power which is 15 watts immediately upon commencement of the ablation procedure until the thermocouples of the needle electrodes sense a temperature of 100° C. within the prostatic tissue. Typically this occurs within one or two seconds, after which the power is ramped down rapidly to a much lower power to maintain the needle electrodes at the approximate 100° C. temperature but not greater than that. Because of the physiology of the human body, the prostatic tissue is different at the proximal needle location versus the distal needle location. Operating in the cold needle mode, the proximal needle pair after the first 15 seconds requires approximately eight watts of power to maintain the approximate 100° C. temperature. On the other hand the power demand at the distal pair of needle electrodes after the first 15 seconds is approximately one-half of that or four watts.

After 30 seconds, the difference in power demand between the distal and proximal pairs becomes less, and after approximately one minute the power demand for both is approximately equal. However, the power demand at the proximal location is still somewhat greater. Thus, it is possible to accommodate the difference in thermal loads by delivering different amounts of power to the two separated proximal and distal pairs. After approximately one minute these power loads converge, making it possible to switch to other modes of operation for other electrode configurations as hereinafter described.

It has been found that by utilizing appropriate switching networks as for example relay networks readily provided by one skilled in the art in the RF generator and controller 16 it is possible to electrically reconfigure the needle electrodes to obtain different current flow patterns for lesion generation. This reconfiguring provides for uniform temperatures among four needles despite having only two adjustable power levels. This is possible since a lesion is created between two needles operating as a pair in bipolar operation, and any two needles can be selected to operate as a pair. The lesion is created by the current flow between the two needles of the pair and in the surrounding areas by thermal conduction. Thus transverse lesions are generated when the forward or distal pair is selected as a pair. Similarly a transverse lesion is created by the rear or proximal pair when they are the designated pair. In such situations where two transverse lesions are created, it is possible that the area between the two pairs may not have been heated enough by conduction to create a continuous lesion. To form a continuous lesion or lesions in this region, the needle electrodes can be connected so that one of the needles in each of the proximal and distal pairs is selected to provide two needles as a selected pair and radio frequency energy is supplied between this same pair to create a lesion extending longitudinally between the two electrodes. Similarly when the other two electrodes from the same two pairs are designated, another longitudinal lesion can be created. Similarly, if needles from each of the proximal and distal pairs are selected which are diagonally across from each other to provide a pair, a lesion is created extending diagonally across the area between the pairs of needle electrodes. Similarly, another diagonal lesion can be created by selecting the other two diagonal electrodes of the two pairs of needle electrodes.

In this manner, all of the prostatic tissue between the four needle electrodes can be ablated to cause a relatively large lesion without redeployment of the needles. As explained, these large lesions can be created merely by selecting different pairs of needle electrodes. Thus it can be seen that the needle pairs can be operated in transverse modes, longitudinal modes and diagonal modes to create the desired size of lesion. Thus, it can be seen that varying amounts of power can be delivered to the four needles with adjustment of the power to four needles by adjusting the power levels on two channels in the generator.

Also by the use of these three modes of operation, the transverse mode, the longitudinal mode and the diagonal mode, it is possible to achieve uniform tissue temperatures and concomitant therewith uniform lesions. To best achieve this uniform temperature, it has been found because there are variations in thermal load within the prostatic urethra, it is best to start in the transverse mode in which the most distal needles are a pair having current pass between each other and the proximal needles are another pair having current passing between each other. After operating in this transverse mode for approximately one minute, the generator and controller 16 is switched into a mode where it scans all four needles and finds the lowest temperature of any two needles and after finding those two needles designates those two needles as a bipolar pair. As soon as the two lowest temperature needles have been ascertained, those two needles are configured electrically so that current will pass between those two needles. In doing this, one of those two needles is brought to the target temperature while the other of the two needles is below the target temperature by typically having a different thermal load than the one needle. A short time later, typically on the order of 30 seconds, the generator and controller 16 again scans the four needle array and looks for two coldest needles to once again form a new bipolar pair. Thereafter a high amount of power is delivered to those two needles to bring them up to temperature until one reaches the target temperature. As can be seen, the generator and controller 16 selectively operates in a transverse mode, a longitudinal mode or a diagonal mode between the two coldest needles after the first minute of operation.

In the case where only one needle of the four needle array is drastically below in temperature than the other three, there is a special mode which can be called the cold needle mode where rather than energizing two channels of the generator, the needles are electrically configured so that three needles are electrically common to each other and the other or cold needle is the active needle. Power is then directed to this single needle to bring it up to temperature while all of the other three needles are electrically common and share the power which is being delivered to the one needle to thereby make it possible to bring the one cold needle up to temperature while not forcing the three remaining needles into over-temperature conditions. In one preferred method of operation, the radio frequency generator and controller 16 is permitted to operate in the cold needle mode only during the last minute of the treatment so as to minimize any undesirable temperature drop in the three common needles. It should be appreciated, however, that the RF generator and controller 16 can operate in the cold needle mode at any time during the treatment and be within the scope of the present invention.

From the foregoing it has been found that it is desirable to operate the RF generator and controller 16 so that it is operating in the transverse mode for the first minute until the temperatures being sensed by the thermocouples in the proximal and distal pairs of needle electrodes converge, after which the RF generator and controller 16 begins scanning for the two coldest needles and operates in the transverse mode, the longitudinal mode or the transverse mode, as required. If such a pair of needle electrodes are below the target temperature, this pair can be brought up to the desired temperature by supplying more power to that pair. At any time during the procedure, and preferably near the end of the procedure, the RF generator and controller 16 can also operate in the cold needle mode. If such a cold needle electrode is located, the controller 16 reconfigures the electrode pairs to deliver more power to that cold needle using the other three needles as ground. The foregoing method can be utilized in any device have three or more electrodes.

From the foregoing, it can be seen that there has been provided a new and improved transurethral apparatus which operates solely in the bipolar mode to create large lesions in a minimum amount of time. The procedure is minimally invasive and the patient can be fully awake during the procedure and only remains uncomfortable for a short period of time. In addition, the apparatus and method makes it possible for the physician to reduce his time required for the procedure. The apparatus and method also has an advantage in that it substantially eliminates multiple deployments of a device for a single lobe. This is particularly desirable because it has been found that it is very difficult to precisely position individual deployments in a single lobe. Typically a single deployment in each lobe is all that is required for treatment of BPH. The apparatus can be configured to operate either in the four-needle electrode mode or in the two-needle electrode mode. It is possible to reconfigure the electrode pairs so that large lesions can be created without the necessity of redeployment of the device. During the procedure, the scope utilized can be deployed to permit viewing of either or both pairs of needles. Accurate and highly responsive temperature controls are utilized in controlling the ablation procedure.

What is claimed:

1. Wherein said probe has a distal extremity which is substantially transparent to light, said transparent distal extremity having sidewise extending spaced-apart proximal and distal pairs of holes for receiving the proximal and distal pairs of needle electrodes, a scope slidably mounted in the passageway and means carried by the proximal extremity of the probe for causing movement of the distal extremity of the scope so that it can be moved from position permitting viewing of the urethra during the time that the probe is being advanced in the urethra and for viewing the proximal and distal pairs of needle electrodes for viewing deployment individually or in unison of the proximal and distal pairs of needle electrodes during deployment of the same.

2. A device as in claim 1, further including means for disabling one of the pairs of needle electrodes, and wherein said means for disabling includes means for grasping said one of the pairs of needle electrodes for causing buckling of the same to prevent further deployment of said one of the pairs of needle electrodes.

3. A device as in claim 2 wherein said means for disabling includes a knob and cam means operated by the knob and filaments coupled to the cam and coupled to the needle electrodes of said one of the pair for causing kinks to be formed in the needle electrodes to cause buckling of the same.

4. A device as in claim 1 wherein said means for advancing and retracting the scope includes a rotatably mounted scroll, a knob engaging the scroll for rotating the scroll, and a flexible elongate element extending from the scroll and coupled to the scope for advancing and retracting the scope.

5. A device as in claim 4 wherein said flexible elongate element of the scroll has a length so that the distal extremity of the scope can be moved from a position distal of the first and second pairs of electrodes and proximal of the distal pair of electrodes and proximal of the proximal pair of electrodes.

6. A device as in claim 5, further including a telescoping assembly, said scope being mounted in said telescoping assembly, said flexible elongate element engaging said telescoping assembly.

7. A device as in claim 6 wherein said telescoping assembly includes first, second and third parts with the second part being telescoped into the first part and the third part being telescoped into the second part, said scope being mounted in the first part.

* * * * *